(12) United States Patent
Whiteley et al.

(10) Patent No.: US 8,197,554 B2
(45) Date of Patent: Jun. 12, 2012

(54) ROTARY ACTUATOR ARRANGEMENT

(75) Inventors: Graham Paul Whiteley, Bath (GB);
Craig Fletcher, Bath (GB)

(73) Assignee: Touch Emas Limited, Livingston (GB)

( * ) Notice: Subject to any disclaimer, the term of this patent is extended or adjusted under 35 U.S.C. 154(b) by 7 days.

(21) Appl. No.: 12/377,540

(22) PCT Filed: Aug. 15, 2007

(86) PCT No.: PCT/GB2007/050493
§ 371 (c)(1),
(2), (4) Date: Feb. 13, 2009

(87) PCT Pub. No.: WO2008/020251
PCT Pub. Date: Feb. 21, 2008

(65) Prior Publication Data
US 2010/0234967 A1  Sep. 16, 2010

(30) Foreign Application Priority Data

Aug. 15, 2006  (GB) .................................. 0616162.4

(51) Int. Cl.
*A61F 2/48* (2006.01)
*A61F 2/58* (2006.01)
(52) U.S. Cl. ................. 623/24; 623/60; 623/62
(58) Field of Classification Search .............. 623/24, 623/57–65; 310/83, 84, 75 D
See application file for complete search history.

(56) References Cited

U.S. PATENT DOCUMENTS

| | | | |
|---|---|---|---|
| 2,983,162 A * | 5/1961 | Walton | ............................. 74/640 |
| 3,751,995 A | 8/1973 | Carlson | |
| 3,883,900 A | 5/1975 | Jerard et al. | |
| 4,044,274 A | 8/1977 | Ohm | |
| 4,398,110 A | 8/1983 | Flinchbaugh et al. | |
| 4,577,127 A | 3/1986 | Ferree et al. | |
| 4,678,952 A | 7/1987 | Peterson et al. | |
| 5,581,166 A | 12/1996 | Eismann et al. | |
| 6,786,112 B2 | 9/2004 | Ruttor | |
| 2002/0135241 A1 | 9/2002 | Kobayashi et al. | |
| 2007/0175681 A1* | 8/2007 | King et al. | .................... 180/65.4 |

FOREIGN PATENT DOCUMENTS

| | | |
|---|---|---|
| DE | 2434834 | 2/1976 |
| DE | 10105814 | 9/2002 |
| EP | 0484173 | 5/1992 |

OTHER PUBLICATIONS

International Search Report for corresponding international application No. PCT/GB2007/050493 (Feb. 25, 2008).

* cited by examiner

*Primary Examiner* — Bruce E Snow
(74) *Attorney, Agent, or Firm* — Marshall, Gerstein & Borun LLP

(57) ABSTRACT

A rotary actuator comprises a motor, gearing connected for driving by the motor, an output drive member and bearings for carrying the output drive member, wherein the gearing comprises wave generator gearing and the gearing is at least partially located radially within the bearings. In addition, an artificial limb member comprises an actuator to effect movement of the limb member, wherein the actuator comprises a motor connected to wave generator gearing.

19 Claims, 10 Drawing Sheets

ROTARY ACTUATOR ARRANGEMENT

This invention relates to a rotary actuator and to an artificial limb member.

For a person who has had an amputation, or who has a congenital limb deficiency, an artificial device may be offered, such device comprising a replacement joint(s) attached to their own remaining limb to overcome their disability. In order for this artificial device to be useful, it is required that many parts are moved in controlled ways about many different axes. Often it is impractical for the limbless person to use the body power from their remaining musculature to motivate these movements, and in these cases it is useful to use an electric motor associated to an appropriate transmission to provide this power in the form of an actuator.

There are various devices commercially available that can simulate limb functions, for example pronation and supination of the wrist, using electric power. Typically, these devices use brushed direct current (dc) motors, connected to epicyclic gears (see e.g. DE 3738607) or spur gears. Although the internal geometry and the magnetic materials used in dc motors play a key part in their power output, a rough measure of a motor's output power may be gained from its volume. Conventional dc brushed motors are usually in the form of a cylinder, where the cylinder length is greater than the diameter. Additionally, spur and epicyclic gears which are fitted inline with these motors to reduce their output speed and increase their output torque, are commonly packaged as thin cylinders. Combined, a dc motor and gearhead package that might be able to directly provide the speeds and torques expected in the replacement of human wrist function would need to be long and thin. This geometry is not ideal as the volume taken by the motor and gearhead cannot be also filled by the user's vestigial limb, meaning these devices are limited to those with shorter remaining limb length.

In addition, directly connecting the load from the hand-side of the device directly through epicyclic gearing is not ideal, as the geometry of common gearheads dictates that tooth interactions are relatively small, as too are the intermediate pinions carrying these gears, resulting in a limit to the practical torque output such components can provide for a given scale.

When designing artificial limb devices, there are other considerations also. It is preferable to the person with the limb deficiency that if they wear an artificial device it has minimal bulk as it is desirable that their artificial device fit within a human limb-like volume or envelope permitting them to wear clothing and not appear abnormal. Additionally, limb deficiencies and amputations occur at varying levels, for example a limbless person may have a limb deficiency occurring at a level very close to their wrist, but may have lost the function of rotation of the wrist and wish this function to be replaced by an artificial device. Clearly, the bulk the artificial device may not encroach into the volume already occupied by the persons remaining limb and it is preferable that the device not extend beyond the volume normally occupied by a human limb. Therefore, it is preferable that the actuator that provides the mechanical replacement for this function is as compact as possible.

Commonly, artificial devices reproducing the functions of a lost limb are suspended from the person's body using either a combination of an externally-worn elastomeric sleeve (see e.g. U.S. Pat. No. 6,706,364) and a rigid glass-reinforced plastic socket, or by a rigid socket and straps extending around the person's body. Therefore, as the device is not suspended directly through the musculoskeletal system like an intact human limb, it is preferable that the artificial device has minimal mass, in fact be lighter than the mass of the body parts it is replacing.

Further to the artificial device appearing statically similar in form to a human limb, it is preferable that the artificial device be able to move at speeds similar to human rate and produce minimal noise in operation, so as not to attract the attention of others and cause embarrassment to the user of the device. Additionally, if the artificial device is to serve as a replacement for a shoulder or elbow body part it may be preferable that when the device is not powered, the limb swings freely under its own weight in a manner similar to the 'freeswing' seen in human upper limbs when walking, see for example CN 2199759Y. These considerations indicate that the actuators at these joints should be very efficient, and be backdriveable. The latter consideration may also provide a safety feature for a high power actuator that is in close body contact with the operator and that will be operated in close proximity with other people.

In order that an artificial device serving as a limb replacement has functional as well as cosmetic value, it is important that the actuators motivating the joints can produce appropriately large torque forces. This consideration, in combination with the need to produce human rate movements, indicates that the actuators motivating the joints need to have relatively large power electrical motors and still need to be very compact.

It is an aim of the present invention to provide a rotary actuator arrangement that overcomes the above problems. This is achieved by the use of a transmission utilising wave generator gearing along with a miniature electric motor coupled together in a highly compact arrangement. Such an arrangement results in a relatively small axial length, low weight and highly efficient actuator when compared to alternative solutions.

In accordance with a first aspect of the present invention there is provided a rotary actuator as set out in the accompanying claims.

In accordance with a second aspect of the present invention, there is provided an artificial limb member as set out in the accompanying claims.

A wave generator is described in U.S. Pat. No. 2,983,162. Such a generator suitable for use with the present invention is manufactured by Harmonic Drive. It comprises three concentrically-arranged components. The outermost component is a circular spline, which is a rigid annulus with teeth on its inner circumferential surface, which is typically held fixed during use. These teeth mesh with teeth on an outer circumferential surface of a flexispline, which is a non-rigid cylindrical "cup-shaped" component that may be deformed in a radial direction. In larger wave generators, the flexispline may instead comprise a flexible toothed band, see for example U.S. Pat. No. 4,099,427. The flexispline in turn fits over, and is held in an elliptical shape by, the wave generator component. This is a thin-raced ball bearing fitted onto an elliptical plug, and serves as a high efficiency torque converter. The wave generator component is typically driven by a motor.

The teeth upon the flexispline are slightly smaller in pitch diameter than the circular spline, and typically has two fewer teeth than the circular spline, although this number may differ depending on the form of the wave generator. The wave generator causes the flexispline to deform into an elliptical shape, such that the teeth of the flexispline engage the circular spline at two opposing regions across the major axis of the ellipse. Typically, several teeth will be meshingly engaged at each of these regions, so that excessive force is not placed upon a single tooth, increasing the output torque capacity.

Rotation of the wave generator causes the teeth-engagement regions to travel with the major elliptical axis. For each 180° clockwise (for the sake of example) rotation of the wave generator, the flexispline rotates anticlockwise by one tooth relative to the circular spline. Each complete clockwise rotation of the wave generator results in the flexispline moving anticlockwise by two teeth from its previous position relative to the circular spline. In this manner, a relatively high rotation input speed and low torque of the wave generator (from a motor output) is converted into a relatively low rotation output speed and high torque of the flexispline.

It can be seen that this arrangement provides accurate, high-torque driving at a pre-determined gear ratio using compact equipment. The need for epicyclic gearing for example is removed.

The present invention enables a compact rotary actuator comprising an electric motor, bearings, a rotary wave generator and complementary meshing teeth arranged long a single axis such that the relative motion between fixtures attached to one end of the axis and fixtures attached to the other end of the axis can be accurately controlled by means of rotating the electric motor.

The motor is preferably a stepper motor or electronically commutated brushless 'flat' or 'pan' style dc motor, for example as known from U.S. Pat. No. 6,472,783. These types of motor permit the power generating volume to be maximised in a package that can be relatively large in diameter whilst relatively short in length, however, this arrangement can be used with a conventionally brushed motor. Together, these motors and this type of transmission, when suitably arranged, prove to be very appropriate for actuators that can replace the function of lost human joints. The examples below show that not only can the invention provide an appropriate actuator for a wrist, variants of the invention can be used widely as modules to replace many functions of the limbs, with the arguments regarding efficiency, minimal weight and bulk, and the increased load capacity of the wave-type transmission over other transmissions being true for these other joints as well.

The background above provides evidence for a need for this type of device in the medical market, however, this is but one of many potential applications where light weight compact rotary control is required. Other applications include CCTV position control, robotics and other machine positioning devices.

The invention will now be described with reference to the accompanying drawings, in which.

Figure 1:
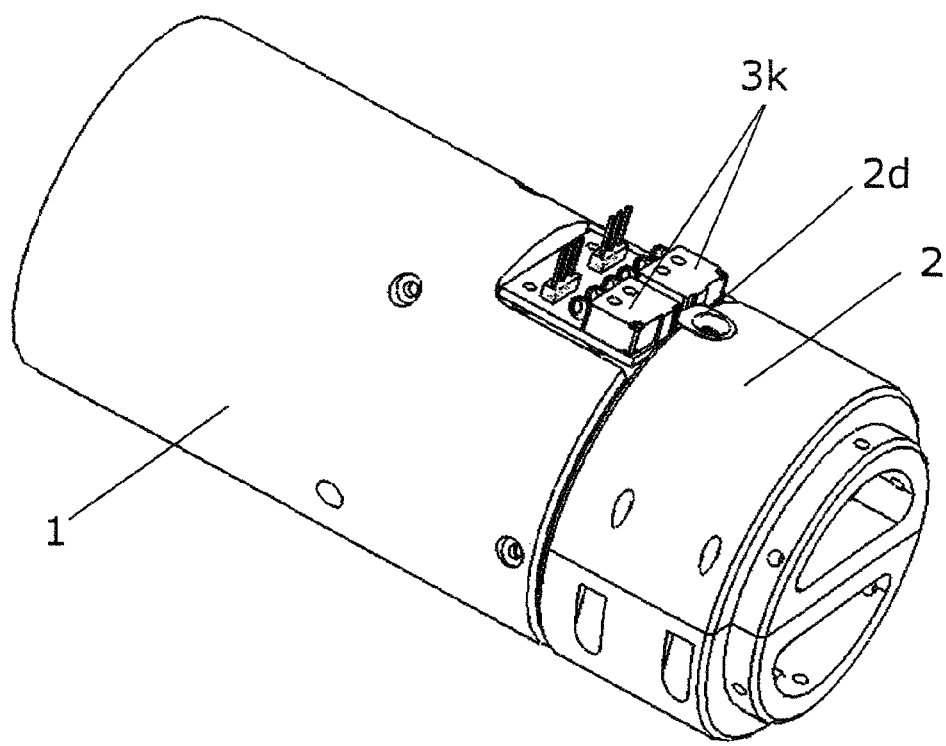
FIG. 1 shows, in perspective, a wrist-actuator arrangement in accordance with a first embodiment of the present invention.
Figure 2:
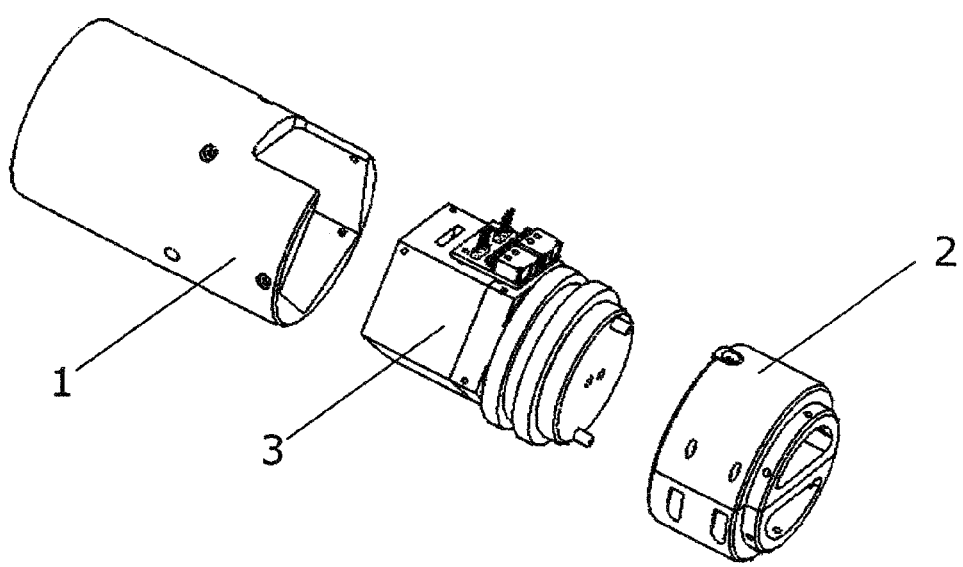
FIG. 2 shows an exploded view of the wrist-actuator arrangement of FIG. 1.

FIG. 1 shows a complete wrist rotation device in accordance with a first embodiment of the present invention. The same device is shown, in exploded view, in FIG. 2. The device comprises a limb socket 1, and artificial hand fixture 2 and a wrist drive unit 3. Position switches 3k and switch dogs 2d are also shown, as will be described later with reference to FIG. 5.

Figure 3:
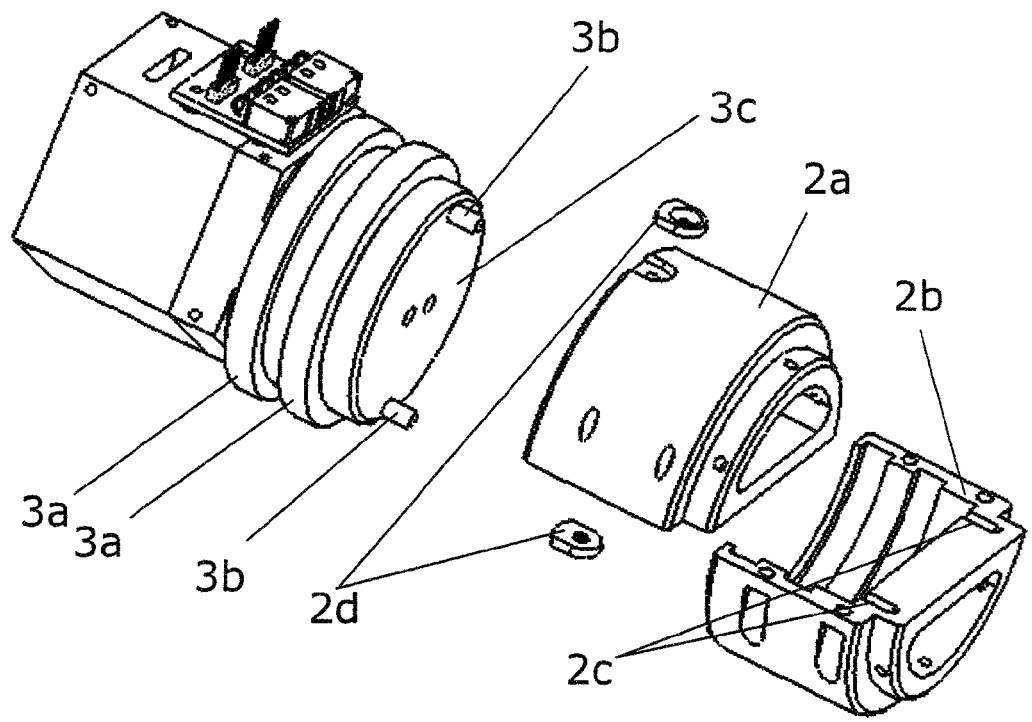
FIG. 3 shows an exploded view of components of the wrist-actuator of FIGS. 1 and 2

FIG. 3 shows the hand fixture 2 and wrist drive unit 3 in an exploded view. The hand fixture 2 is separable into two matching halves 2a and 2b. These halves are joined around two similar bearings 3a that are connected rigidly via their inner bearing races to the wrist drive unit 3. The wrist drive unit 3 comprises driving dowels 3b located on a drive plate 3c, dowels 3b in use being situated within slots 2c located on halves 2a and 2b. In use, the hand fixture halves 2a and 2b are connected together around these features, such that the hand fixture 2 may be driven by the drive plate 3c via dowels 3b to rotate the hand fixture 2 relative to both the limb socket 1 and wrist drive unit 3.

Figure 4:
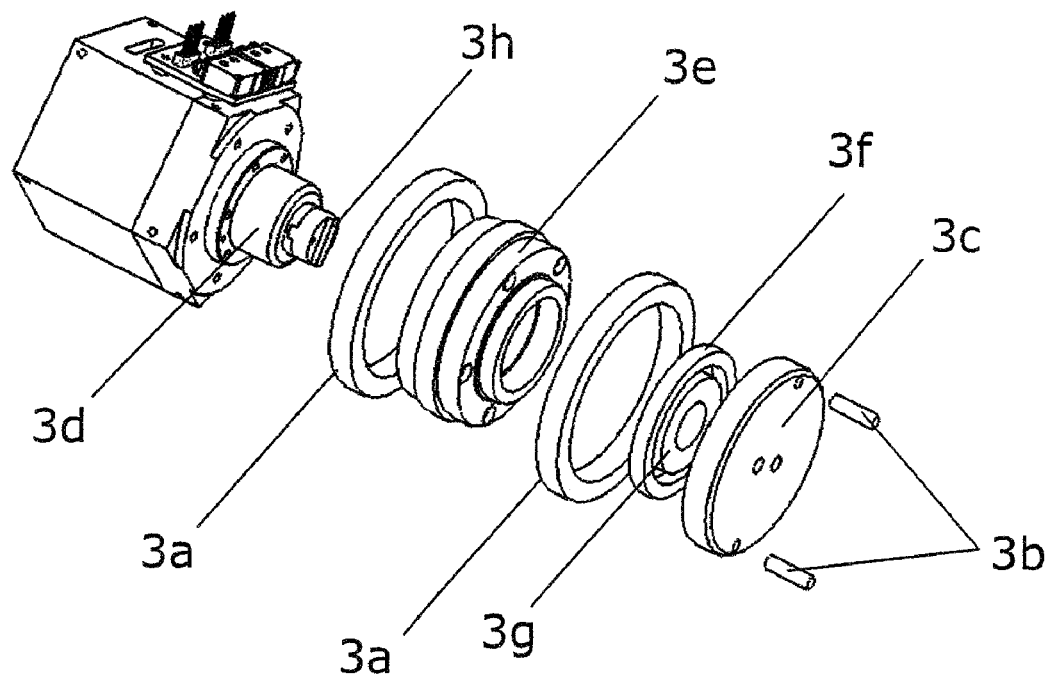
FIG. 4 shows an exploded view of components of the wrist-actuator of FIGS. 1-3.

FIG. 4 shows the wrist drive unit 3 in an exploded view. Bearings 3a are secured around a bearing boss 3e that surrounds a wave drive component 3d. The bearing boss 3e is rigidly connected to the remaining structure of the wrist drive unit 3 through a series of radially arranged threaded fasteners (not shown). A driving dog 3h, with threaded fasteners (not shown), is connected to the output of the wave generator 3d to communicate torque from wave generator 3d to the drive plate 3c. A bearing 3g is positioned radially between the driving dog 3h and the bearing boss 3e, while a second concentrically arranged bearing 3f is positioned radially between the bearing boss 3e and the drive plate 3c. Bearings 3f and 3c in use ensure the concentric and efficient operation of the wave generator 3d in supplying torque to hand fixture 2.

Figure 5:
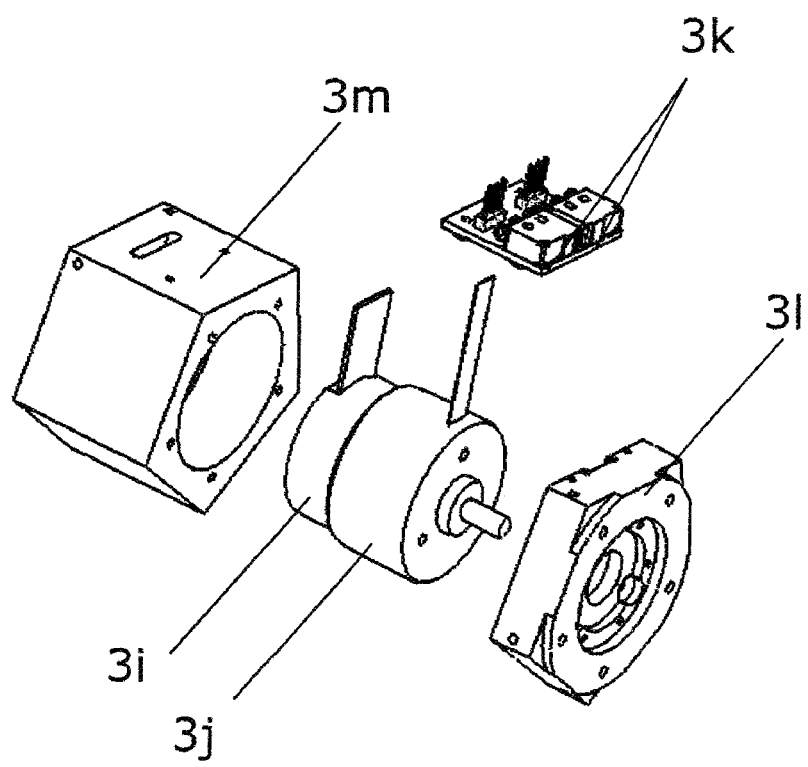
FIG. 5 shows an exploded view of components of the wrist-actuator of FIGS. 1-4.

FIG. 5 shows the electrical power stage components of the wrist drive unit 3 in an exploded view. An electrical motor 3j is held within the wrist drive unit 3, this motor 3j being fitted with an optical encoder 3i. The electrical motor 3j is fixed within the wrist drive unit 3 through threaded fasteners (not shown) that affix the motor 3j to a motor flange 3l. Motor flange 3l is further affixed to a motor case 3m to encase the motor 3j and encoder 3i within the wrist drive unit 3. Both the motor flange 3l and the motor case 3m have an exterior geometry, in this case a hexagonal cross-section, that permits no relative rotation between the limb socket 1 and themselves when the limb socket 1 is in place covering them. Position switches 3k are rigidly connected to the motor case 3m and motor flange 3l. Switch dogs 2d (see FIG. 1) are rigidly connected to hand fixture 2 for co-operation with respective position switches 3k. In use, when the hand fixture 2 is rotated, a switch 3k is depressed by its corresponding switch dog 2d. In combination with the encoder 3i, this enables the absolute position of the joint to be deduced by electronic driving circuitry (not shown).

FIGS. 6 to 10 show a wrist actuator according to second embodiment of the present invention. The actuator comprises two subassemblies 4 and 5, that move relatively to one another. In the embodiment shown, subassembly 5 is designed to be attached to a vestigial forearm, while subassembly 4 is designed to carry an artificial hand. A lug 4a is mounted on subassembly 4 for co-operation with microswitches 5a, mounted on subassembly 5. An encoder 5b is also mounted on subassembly 5. These components enable subtle control of the actuator through the instrumenting and electronic detection of the relative movement between subassemblies 4 and 5. Using these microswitches as limit-of-movement switches, the encoder can very accurately count revolutions between these movement extents and so determine the position of the actuator. Motor 5n (see FIGS. 9, 10) is housed within subassembly 5. It is generally preferable to situate the microswitches 5a, encoder 5b and motor 5n on the same relative side of the actuator as this means electrical wiring does not have to bridge between the two relatively moving sides of the actuator. Subassembly 4 includes at its distal end a fixture 4b for carrying an artificial hand (not shown). Subassembly 4 is supported in a cantilever manner through two bearings 4c that fit into mating grooves 4d in subassembly 4 and around grooves 5c in annulus 5d. A torque transmission plate 4e is the final component that transmits torque from subassembly 5 to subassembly 4, it comprises a slot 4f for engagement with a tenon 5e in drive component 5f (see FIG. 8).

Figure 6:
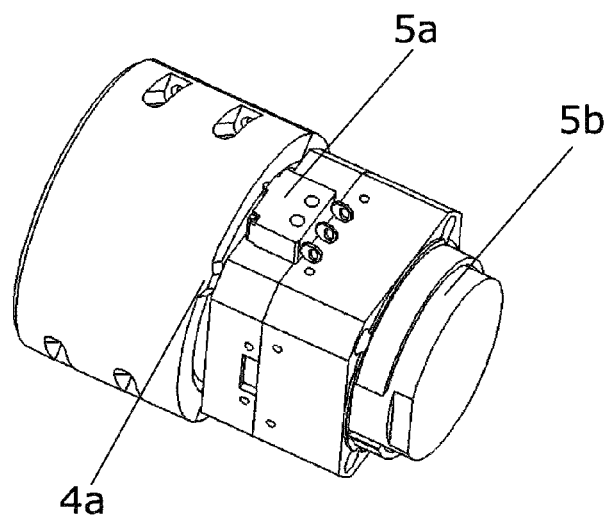
FIG. 6 shows a complete wrist actuator unit in accordance with a second embodiment of the present invention in perspective view.
Figure 7:
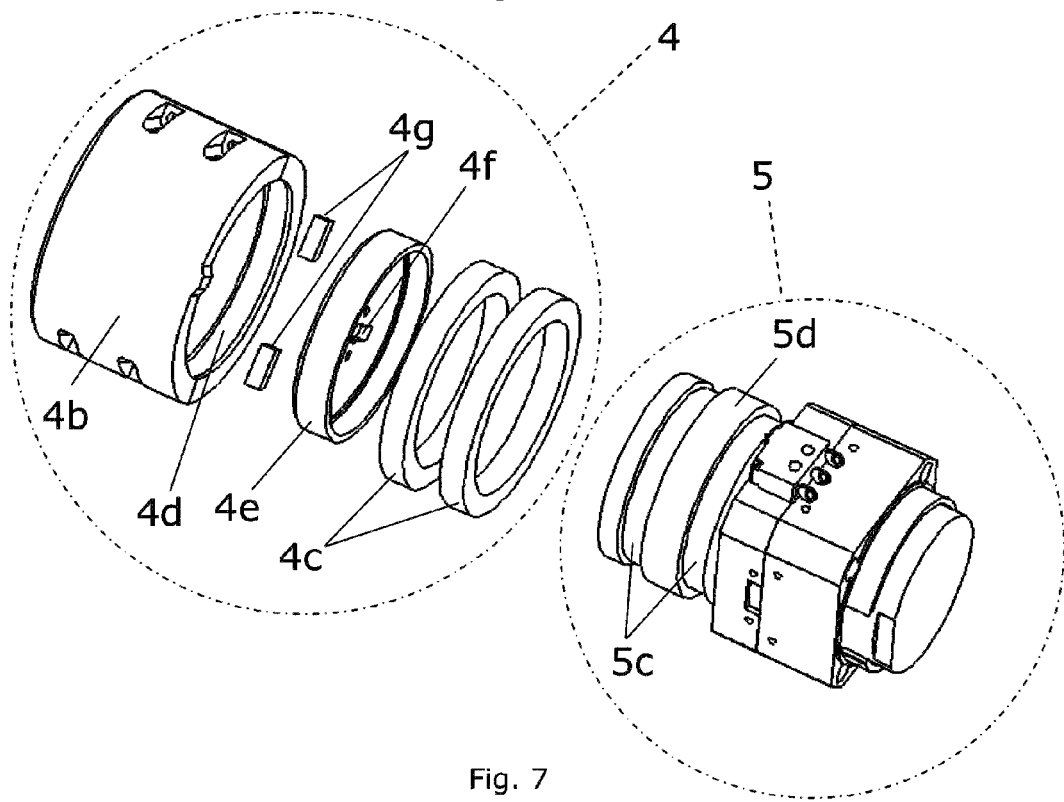
FIG. 7 shows the wrist actuator arrangement of FIG. 6 in an exploded view.
Figure 8:
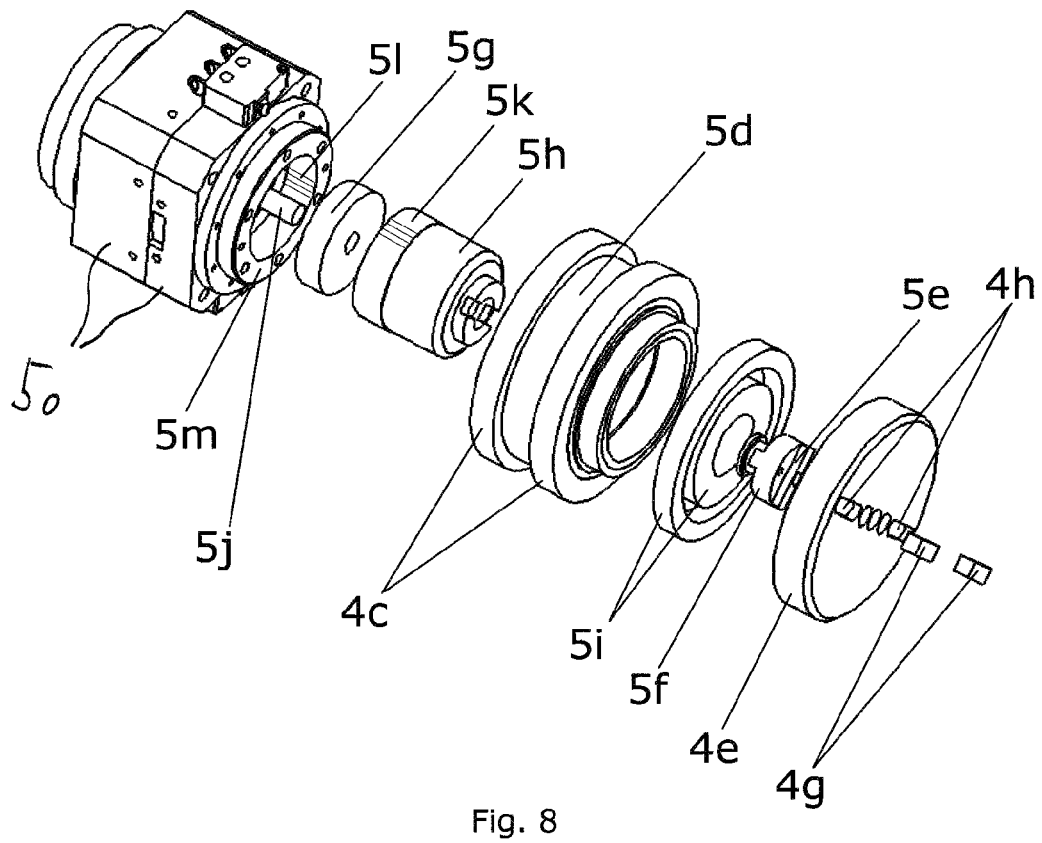
FIG. 8 shows, in an exploded view, components of the actuator arrangement of FIGS. 6 and 7.

FIG. 8 shows the torque transmission arrangement for the actuator, from a different perspective to FIGS. 6 and 7, i.e. with the subassembly 4 foremost, enabling the wave generator components to be identified. Torque transmission is provided to fixture 4b via key steels 4g which fit both into matching slots 4h in transmission plate 4e and corresponding matching slots in fixture 4b (not shown). The driving subassembly 5 comprises the drive component 5f, with its associated tenon 5e, constrained within concentrically-arranged bearings 5i. Drive component 5f is connected in turn to a flexispline 5h driven by a wave generator 5g. The wave generator is connected to, and driven by, a motor pinion 5j. Flexispline 5h has miniature teeth 5k on its periphery, which engage with circular spline 5m mounted on a housing 5o (see FIG. 9) of the subassembly 5.

This transmission arrangement improves the efficiency and reliability of the actuator by reducing any force components, other than torque, being transmitted back to the elliptical wave generator 5g, and flexispline 5h parts of the gearing. In addition, concentrically arranged bearings 5i constrain drive component 5f both axially and angularly to ensure that this component only transmits torque forces to the flexispline 5h part of the transmission.

In operation the motor pinion 5j transmits torque and high speed rotation to the elliptical wave generator 5g, this component deforms the flexispline 5h in a controlled manner whereby miniature teeth on its periphery 5k will index two teeth, relative to the teeth 5l on the circular spline 5m, for every revolution of the elliptical wave generator 5g. The slower speed and higher torque rotation of the flexispline 5h is then transmitted to the moving subassembly 4 through the tenon 5e and slot details described above. In addition to the benefits of the high efficiency of the wave generator-type gear transmission, in operation there are always many gear teeth 5k, 5l in mesh at any instant, therefore, increasing its output torque capacity over other gearing schemes.

Figure 9:
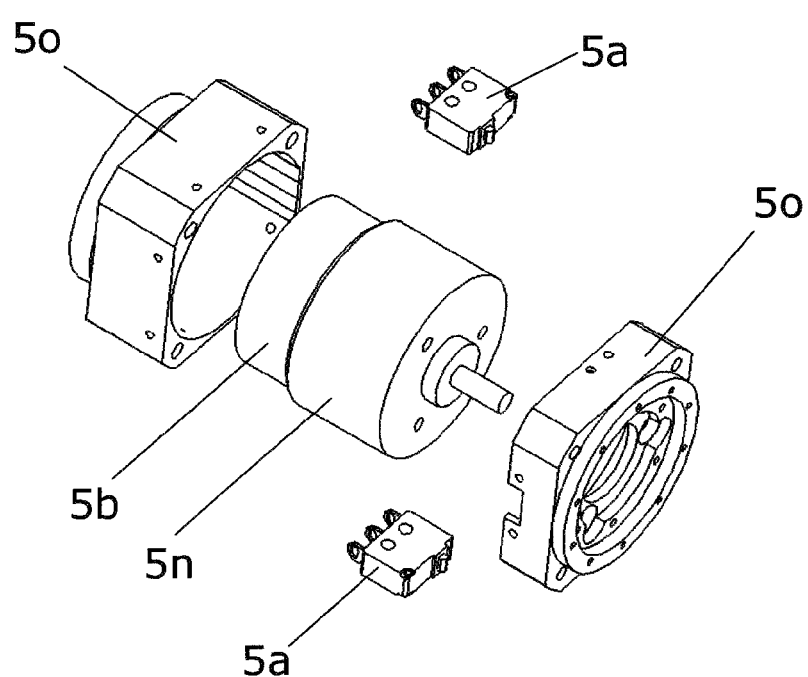
FIG. 9 shows, in an exploded view, components of the actuator arrangement of FIGS. 6-8.

As shown in FIG. 9, the motor 5n, encoder 5b and microswitches 5a, necessary for subtle control, are all situated on one side of the actuator, reducing the need for electrical wiring spanning the relatively moving subassemblies. The motor 5n and encoder 5b are retained within housings 5o, which are prismatic to prevent the unit twisting in reaction to any applied loads on the moving subassembly 4.

Figure 10:
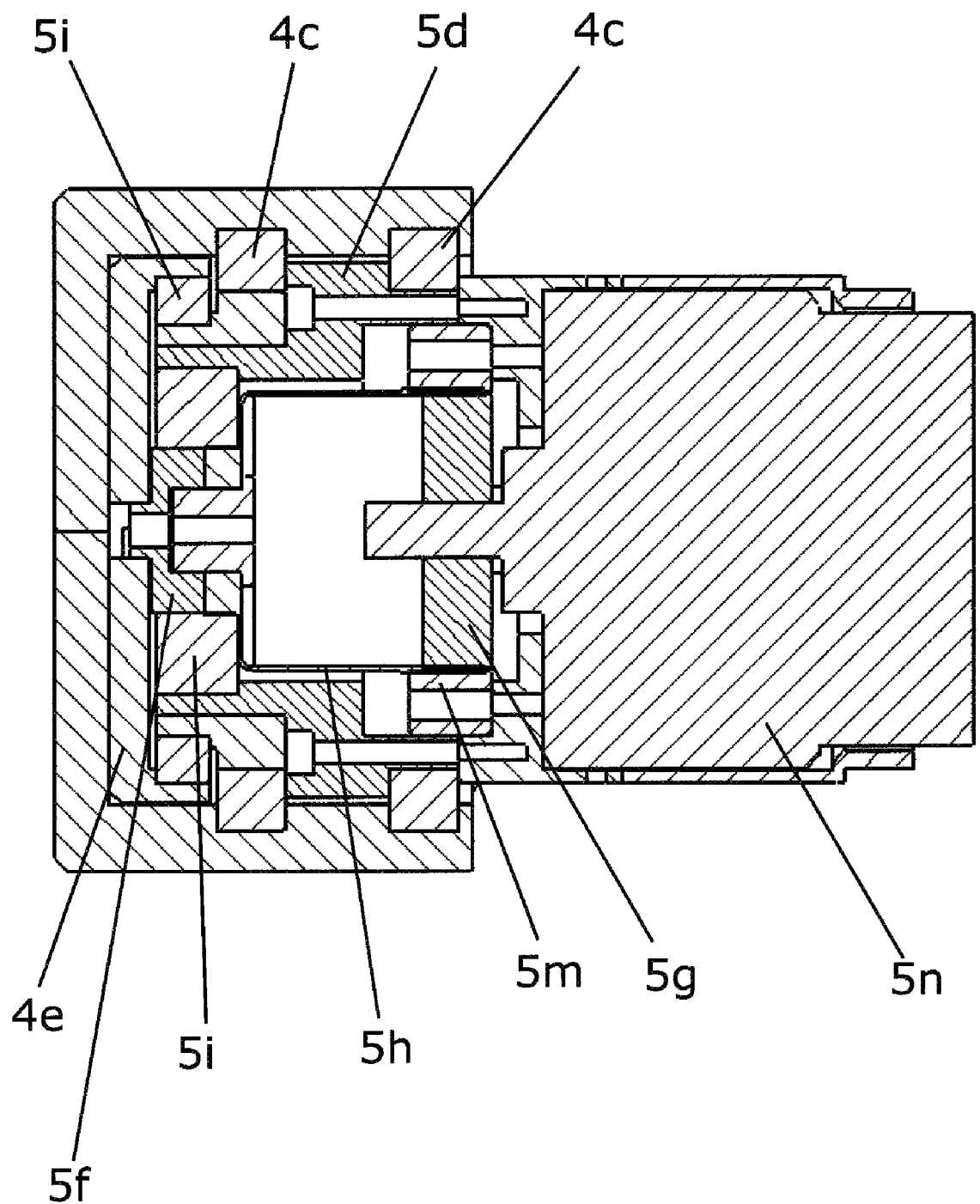
FIG. 10 shows a sectional view of the actuator of FIGS. 6-9.
Figures 11, 12:
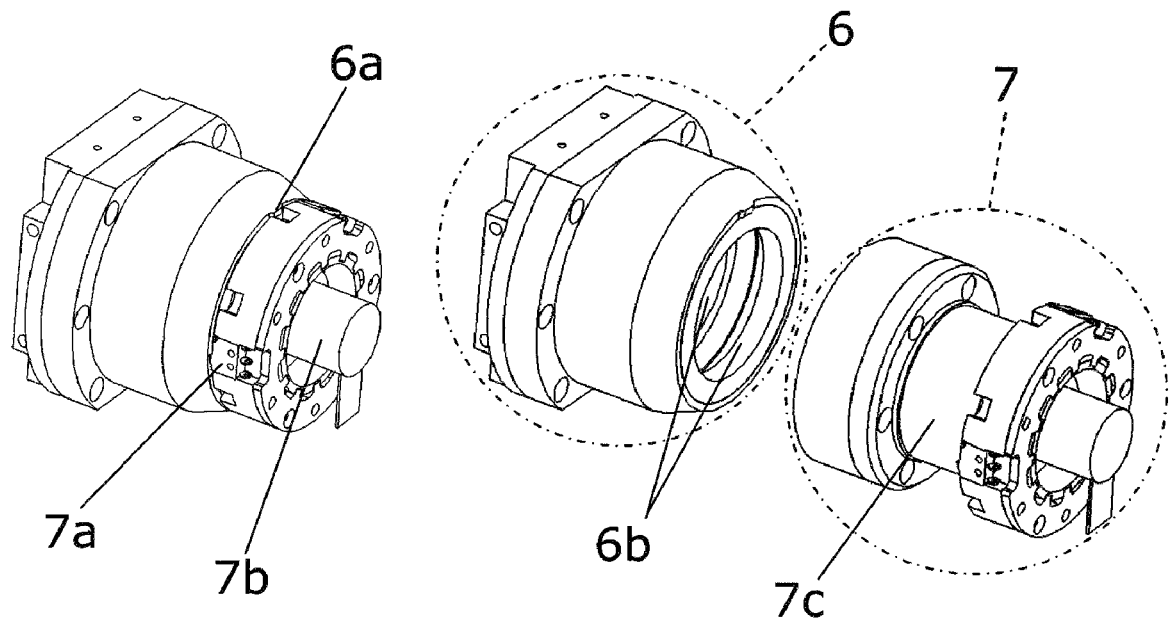
FIG. 11 shows, in perspective view, a shoulder actuator unit in accordance with a third embodiment of the present invention.
FIG. 12 shows, in an exploded view, components of the unit of FIG. 11.
Figure 13:
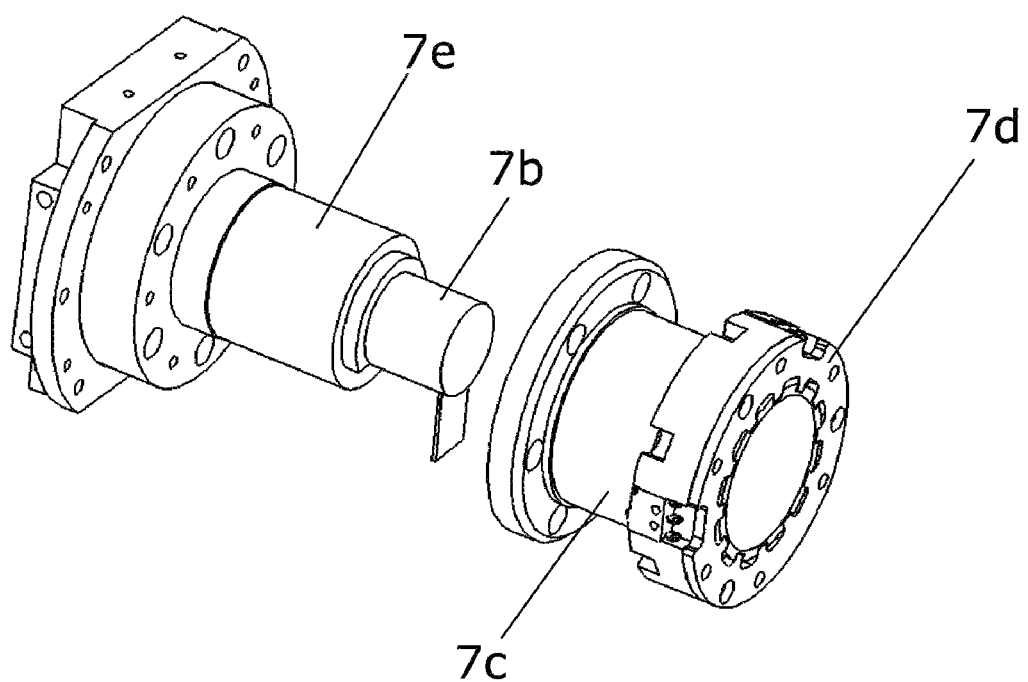
FIG. 13 shows, in an exploded view, components of the unit of FIG. 11.

FIG. 10 shows a sectional view of the wrist actuator. It can be seen that the bearings 4c, 5i, transmission components 4e, 5f, 5h, 5g and 5m and motor 5n are nested so as to provide a compact arrangement.

While the embodiment described shows fixture 4b for carrying an artificial hand, it is possible, if volume is made available in the design of an artificial hand (not shown) for the actuator subassembly 5, that component 4b may be connected to the forearm of an artificial arm. In this case, subassembly 4 would be fixed, while subassembly 5 would rotate relative to subassembly 4.

Figure 14:
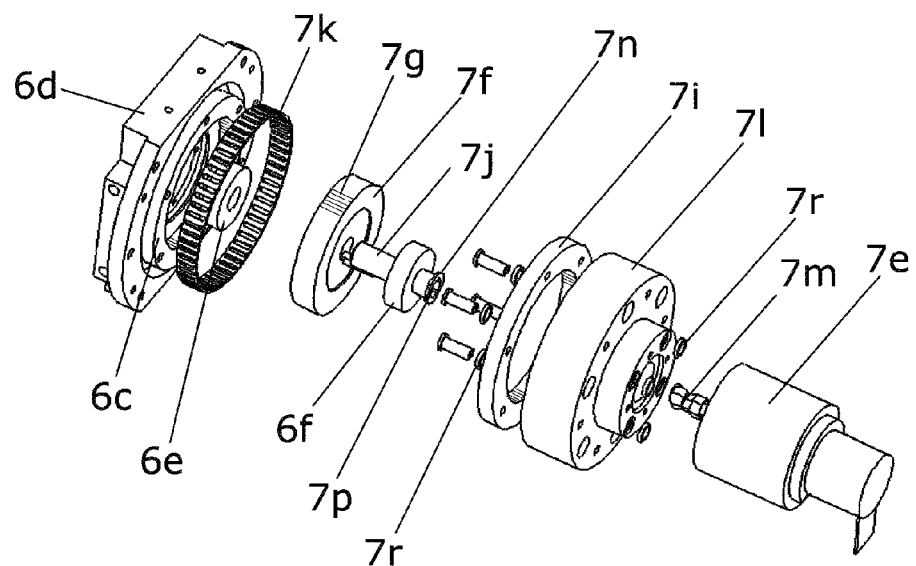
FIG. 14 shows, in an exploded view, the components of FIG. 12.
Figure 15:
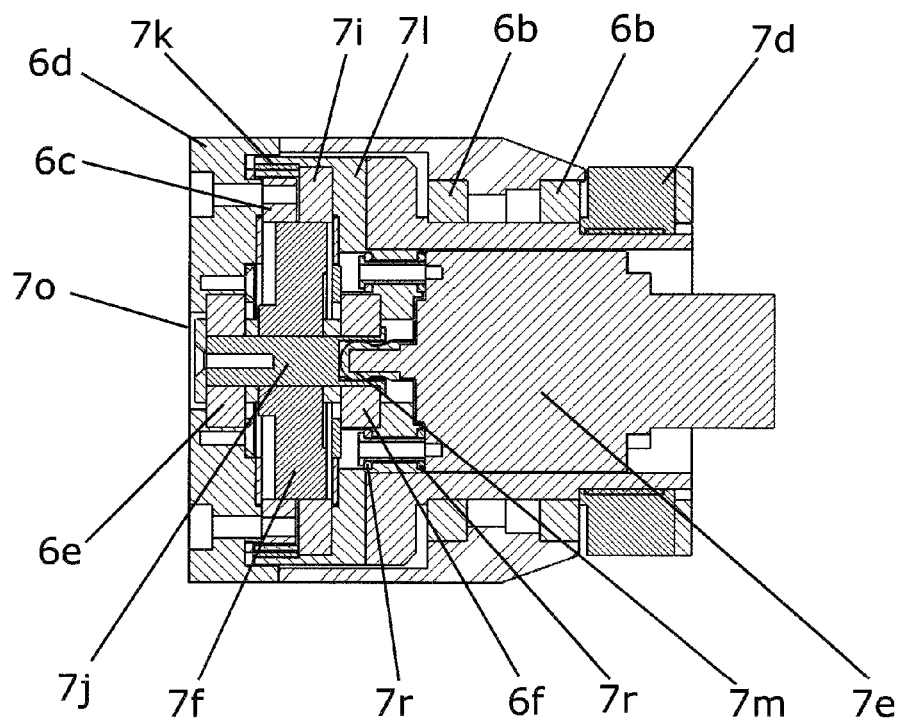
FIG. 15 shows a sectional view of the unit of FIGS. 11 to 14.

FIGS. 11 to 14 variously show, in exploded, perspective views, a third embodiment of the present invention in which the actuator arrangement is used as a shoulder flexing actuator, with a sectional view shown in FIG. 15. This application requires greater size and power output than the wrist actuators described above. The shoulder actuator comprises two relatively movable subassemblies 6 and 7, with subassembly 6 fixed and subassembly 7 movable. Similarly to the wrist actuator embodiment shown in FIGS. 6 to 10, a combination of a lug 6a with microswitches 7a is used as limit switches. These switches are used in conjunction with a motor encoder 7b mounted on a motor 7e to electronically determine the rotational position of the actuator. The arrangement of microswitches 7a, encoder 7b and motor 7e wiring on the same subassembly side of the actuator reduce wiring spanning the moving parts of the actuator. Similarly to the wrist actuator embodiments, the arrangement of bearings 6b about a hollow shaft 7c is appropriate to support a cantilever load, in this example from a pitch circle of holes on a flange 7d fixed to the shaft 7c. Similarly to the wrist actuator embodiments, the arrangement of bearings 6b is nested to surround the transmission, however, with the shoulder actuator the bearings also nest concentrically around the motor 7e. This is made possible due to the increase in the size of the anatomical envelope available at the shoulder. This arrangement is shown more clearly in FIG. 13. It can be seen that the motor 7e and motor encoder 7b fit within the centre of the hollow shaft 7c, such that they are surrounded by bearings 6b.

FIG. 14 shows details of the transmission. The increase in the anatomical envelope at the shoulder allows the use of a wave generator-type drive with increased diameter, but which is relatively shorter in length than that used at the wrist. This type of wave-generated transmission uses a similar elliptical wave generator 7f, however, in this case a flexible band of teeth 7g is used rather than a "cup-shaped" flexispline, such that the band 7g fits onto the wave generator 7f and is thus deformed into an alliptical shape. In the operation of this type of wave-generated transmission, there are two rings of teeth 6c and 7i, of which one, 7i, has a similar number of teeth to the flexible band 7g, whilst the other ring 6c differs by one tooth. The rings 6c and 7i are constrained concentrically about a wave generator shaft 7j. In operation, when the elliptical wave generator 7f revolves one revolution, the circular toothed ring 6c is seen to index one tooth relatively to the circular ring 7i with a similar number of teeth 7i. The output transmission is taken from one of two circular rings of teeth 6c, 7i, in this case ring 6c. The concentric constraint of the two circular toothed rings, 6c and 7i is critical, and is achieved through a bearing 7k running on an outer perimeter of the toothed ring 6c and against a flange 7l that has toothed ring 7i centrically mounted within it. Flange 7l and a flange 6d have recesses concentric to the toothed rings 6c, 7i for the placement of bearings 6e, 7f that permit the concentric rotation of wave generator shaft 7j. Shaft 7j is connected for rotation with a motor pinion 7m, driven by motor 7e, and rotation of shaft 7j rotates the wave generator 7f. Shaft 7j is carried within bearings 6e and 6f, and has an end flange 7n.

Within this larger scale actuator there are higher torques, vibrations and other forces acting within the actuator and it is important that any unwanted forces are not transmitted back through to the driving motor pinion 7m. Preventing the transmission of these forces is achieved by a combination of the following features:

(i) The wave generator shaft 7j is constrained so as not to translate axially by flange 7n and a cap 7o that are secured against bearings 6e, 6f.

(ii) The motor pinion has a ball-type hex key design male mating 7m fitting within a matching female hexagonal socket 7p in the wave generator shaft 7j. The effective spherical centre of the ball type hex design 7m approximately corresponds to the centre of the wave generator bearing 6f. In this way, any misalignment of the wave generator shaft 7j that may be generated under high torques or accelerations/decelerations in the wave-type drive is not transferred to the motor pinion 7m.

(iii) The motor 7e and motor pinion 7m are flexibly supported against the flange 7l through resilient, in this case rubber, mountings 7r. These rubber mountings permit the motor 7e and motor pinion 7m to deflect slightly should there be any off-axis forces transmitted through the transmission. Additionally, the rubber mountings help to prevent any damaging vibrations generated by rotating the elliptical wave generator 7f at high speed being transmitted through to the motor pinion 7m and motor 7e.

FIG. 15 shows a sectional view of the actuator. The nested nature of the load carrying bearings 6b about the transmission and motor components can be clearly seen.

Figure 16:
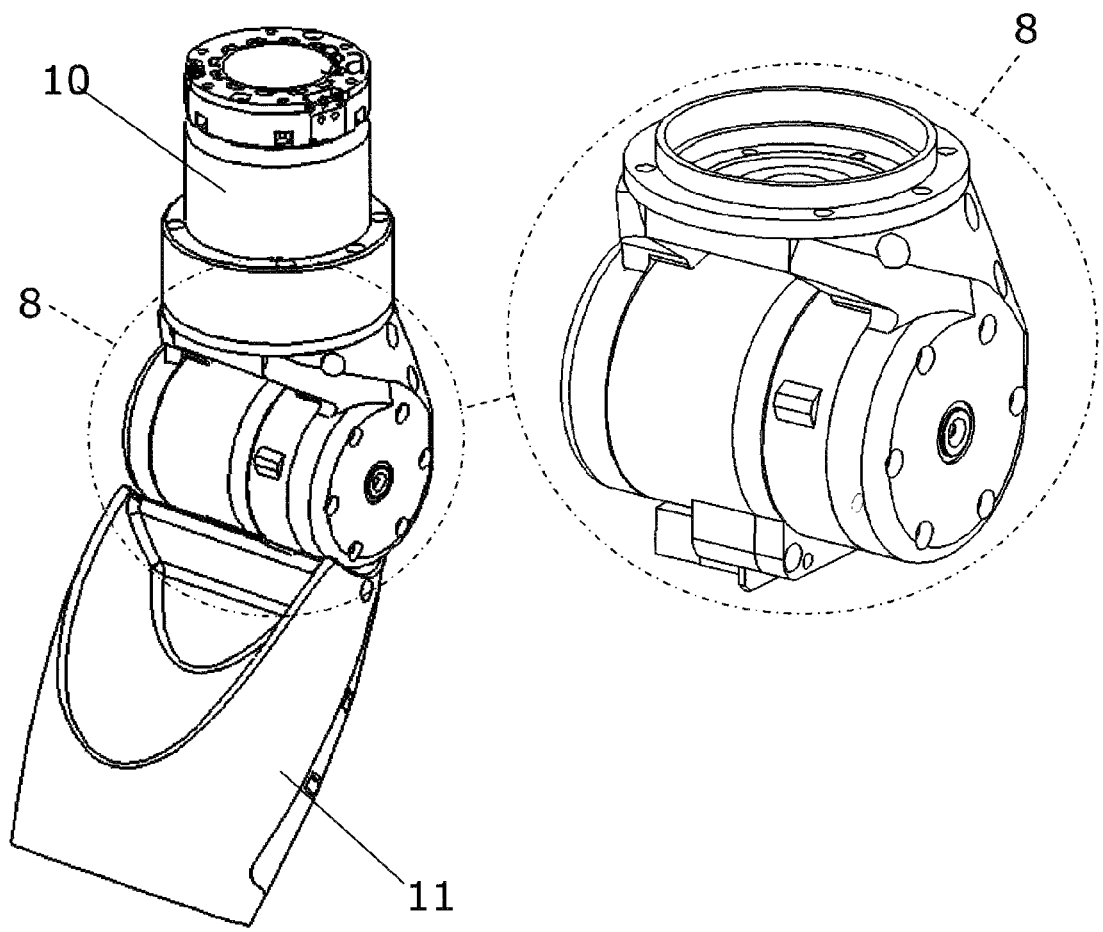
FIG. 16 shows in perspective view, a humeral rotator actuator and elbow flexor actuator in accordance with a fourth embodiment of the present invention.
Figure 17:
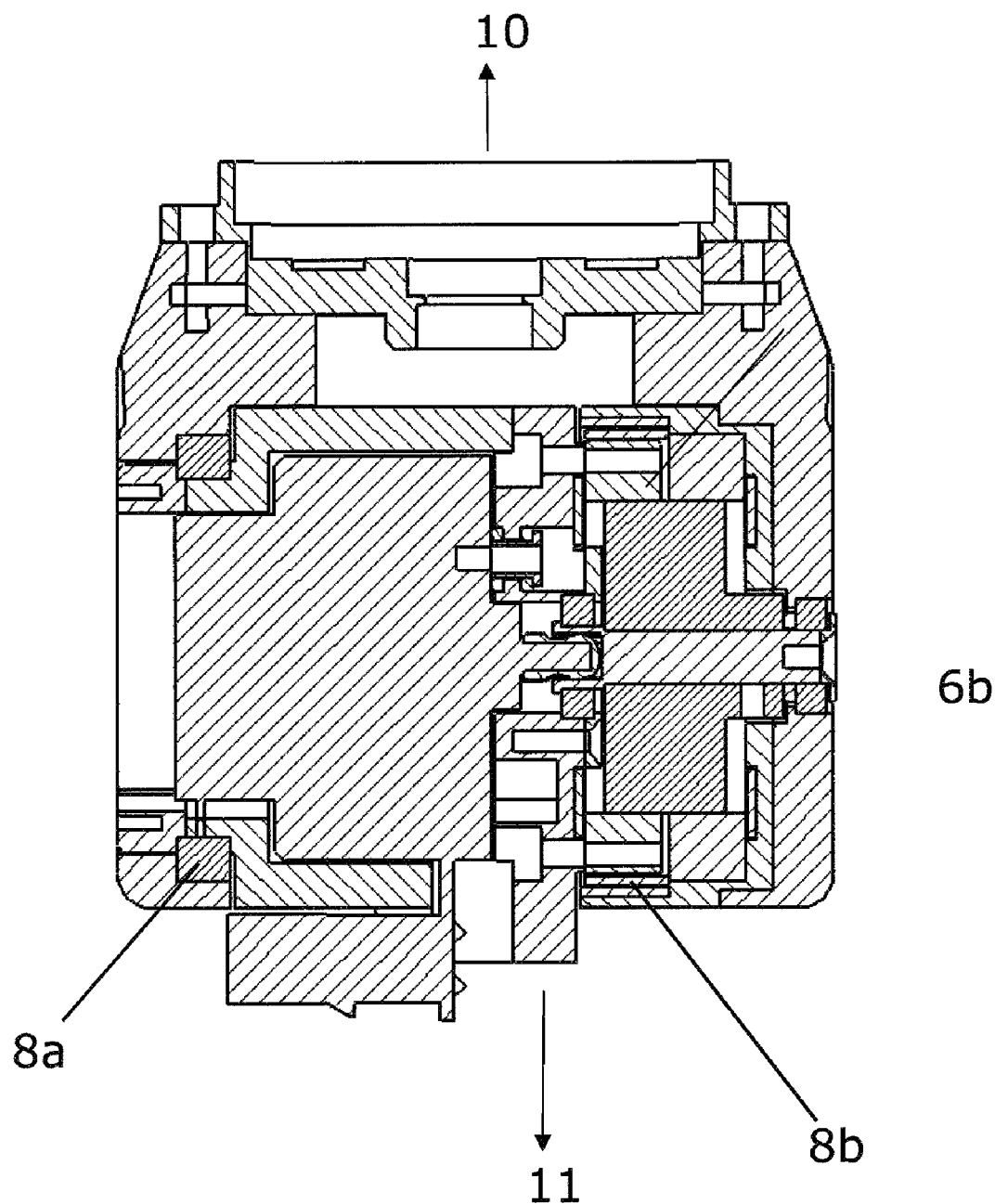
FIG. 17 shows a sectional view unit of FIG. 16.

A fourth embodiment of the present invention, in which the actuator arrangement is used in an elbow-flexing actuator, is shown in FIGS. 16 and 17. Looking firstly at FIG. 16, which shows a perspective view, the elbow-flexing actuator comprises two actuators 8 and 10, each in accordance with the present invention, arranged at right angles. The upper actuator 10 is an actuator for humeral rotation, enabling the lower actuator 8 and a limb section 11 below it to twist towards and away from the body. The humeral rotator actuator 10 has bearings (not shown) appropriately arranged to support the sections above and below it in a cantilever fashion. This arrangement is similar to that already described with reference to the shoulder actuator of the third embodiment and need not be described explicitly further. The actuator below the humeral rotator actuator 10 is an elbow flexing actuator 8. This is generally similar to the actuator of the third embodiment described above and need not be described in depth, however here the bearing arrangement supports the limb section 11 below it. FIG. 17 shows a sectional view of the elbow-flexing actuator 8 showing the different bearing arrangement. A deep-groove ball bearing 8a and a needle roller race 8b support loads 10 above and 11 below it. Limb section 11 is connected to a radial extension of the motor unit, while the upper arm section is connected to the wave generator output.

The examples described above show how the actuator arrangement can be widely used in a modular fashion, at different scales, and with different load carrying bearing arrangements to reproduce many of the functions of human limbs.

The invention is not limited to the above-described embodiments, and many other variations are possible within the scope of the claims.

For example, many instrumentation schemes may be used. Similar results may be achieved using optical or magnetic switches, or by using absolute encoders that directly determine position through magnetic field strength or and analogue signal level, or other counting schemes.

The actuator may be used for applications other than artificial limb parts. For example, it may find application in CCTV camera control, robotics or other machine positioning areas.

The invention claimed is:

1. An artificial limb member comprising an actuator to effect movement of the limb member, wherein the actuator comprises:
   wave generator gearing;
   a motor for causing rotation about an axis, the motor connected to the wave generator gearing;
   a first toothed ring driven by the motor; and
   bearings for carrying the first toothed ring;
   wherein the actuator comprises a second toothed ring, the first and second toothed rings being circular, with the bearings carried between the first and second toothed rings, and the wave generator gearing is at least partially located radially within the bearings such that the bearings run on an outer perimeter of the first, circular toothed ring providing concentric constraint of the first, circular toothed ring.

2. A limb member according to claim 1, comprising resilient mounting to enable the motor to deflect from its driving axis.

3. A limb member according to claim 1, comprising an encoder for determining the rotational position of the actuator.

4. A limb member according to claim 1, comprising a limit switch for indicating the maximum range of rotation of the actuator.

5. An artificial limb member comprising an actuator to effect movement of the limb member, wherein the actuator comprises:
   wave generator gearing;
   a shaft for driving the gearing;
   a motor for causing rotation about an axis, the motor connected to the wave generator gearing;
   a toothed ring driven by the motor; and
   bearings for carrying the toothed ring;
   wherein the wave generator gearing is at least partially located radially within the bearings such that the bearings run on an outer perimeter of the toothed ring providing concentric constraint of the toothed ring; and
   wherein the motor is coupled to the shaft via a keyed spherically-formed male mating socket engaging with a matching keyed female socket.

6. A limb member according to claim 5, wherein the male mating is located substantially at the centre of the gearing.

7. A limb member according to claim 5, comprising means for preventing the axial translation of the shaft.

8. A limb member according to claim 7, wherein the axial translation prevention means includes a flange mounted on the shaft.

9. A limb member according to claim 5, wherein the male and female sockets are hexagonal.

10. An artificial limb member comprising an actuator to effect movement of the limb member, wherein the actuator comprises:
- wave generator gearing;
- a motor for causing rotation about an axis, the motor connected to the wave generator gearing;
- a toothed ring driven by the motor; and
- bearings for carrying the toothed ring;
- wherein the wave generator gearing is at least partially located radially within the bearings; the actuator comprises a shaft for driving the gearing, and the motor is coupled to the shaft via a keyed spherically-formed male mating socket engaging with a matching keyed female socket.

11. A limb member according to claim 10, wherein the male and female sockets are hexagonal.

12. A limb member according to claim 10, wherein the male mating is located substantially at the centre of the gearing.

13. A limb member according to claim 10, comprising means for preventing the axial translation of the shaft.

14. A limb member according to claim 13, wherein the axial translation prevention means includes a flange mounted on the shaft.

15. A limb member according to claim 10, comprising resilient mounting to enable the motor to deflect from its driving axis.

16. A limb member according to claim 10, comprising an encoder for determining the rotational position of the actuator.

17. A limb member according to claim 10, comprising a limit switch for indicating the maximum range of rotation of the actuator.

18. An artificial limb member comprising an actuator to effect movement of the limb member, wherein the actuator comprises:
- wave generator gearing;
- a motor for causing rotation about an axis, the motor connected to the wave generator gearing;
- a toothed ring driven by the motor; and
- bearings for carrying the toothed ring;
- wherein the wave generator gearing is at least partially located radially within the bearings such that the bearings run on an outer perimeter of the toothed ring;
- wherein the actuator comprises a shaft for driving the gearing;
- wherein the motor is coupled to the shaft via a spherically-formed male mating socket engaging with a matching female socket; and
- wherein the male and female sockets are hexagonal.

19. An artificial limb member comprising an actuator to effect movement of the limb member, wherein the actuator comprises:
- wave generator gearing;
- a motor for causing rotation about an axis, the motor connected to the wave generator gearing;
- a toothed ring driven by the motor; and
- bearings for carrying the toothed ring;
- wherein the wave generator gearing is at least partially located radially within the bearings; the actuator comprises a shaft for driving the gearing, and the motor is coupled to the shaft via a spherically-formed male mating socket engaging with a matching female socket; and
- wherein the male and female sockets are hexagonal.

* * * * *